(12) United States Patent
Bley

(10) Patent No.: US 6,306,418 B1
(45) Date of Patent: Oct. 23, 2001

(54) CONTROLLED EXPANSION SPHINCTER AUGMENTATION MEDIA

(76) Inventor: Robert Steven Bley, 298 Stanford Ave., Menlo Park, San Mateo County, CA (US) 94025

( * ) Notice: Subject to any disclaimer, the term of this patent is extended or adjusted under 35 U.S.C. 154(b) by 0 days.

(21) Appl. No.: 08/279,569

(22) Filed: Jul. 25, 1994

Related U.S. Application Data

(62) Division of application No. 07/935,151, filed on Aug. 20, 1992.

(51) Int. Cl.$^7$ ................................................ A61F 13/00
(52) U.S. Cl. ......................... 424/422; 424/423; 424/489
(58) Field of Search .................................. 424/489, 423; 600/29, 31; 604/51

(56) References Cited

U.S. PATENT DOCUMENTS

| Re. 32,969 | * | 6/1989 | Trager et al. | 514/912 |
|---|---|---|---|---|
| 4,272,518 | | 6/1981 | Moro et al. . | |
| 4,773,393 | * | 9/1988 | Haber et al. | 600/30 |
| 4,777,200 | * | 10/1988 | Symond et al. | 524/458 |
| 4,803,075 | * | 2/1989 | Wallace et al. | 424/423 |
| 5,007,940 | * | 4/1991 | Berg | 424/423 |
| 5,067,965 | * | 11/1991 | Ersek et al. | 623/66 |
| 5,336,263 | * | 8/1994 | Ersek et al. | 600/29 |

FOREIGN PATENT DOCUMENTS

| A-0 251 695 | 6/1987 | (EP) . |
|---|---|---|
| WO-A-86 01813 | 3/1986 | (WO) . |
| WO-A-93 16658 | 9/1993 | (WO) . |
| WO-A-93 19702 | 10/1993 | (WO) . |

OTHER PUBLICATIONS

Aesthetic Plastic Surgery, vol. 16, no. 1, 1992 NY, USA, pp. 59–65, Author R.A. Ersek et al, Title Bioplastique : A New Biphasic Polymer for Minimally Invasive Injection Implantation.

* cited by examiner

*Primary Examiner*—Thurman K. Page
*Assistant Examiner*—Liliana DiNola-Baron

(57) ABSTRACT

A composition for injecting into tissues surrounding the urethra or ureter. It comprises a plurality of physiologically acceptable solid polymer particles dispersed in a physiologically acceptable biodissipatable liquid carrier. The polymer comprises a hydrophilic component and may also include a non-hydrophilic component. The polymer hydrates and swells to a predetermined volume as the liquid carrier dissipates. The composition is especially suitable in treating patients with urinary incontinence and patients with vesicoureteral reflux via injection into the tissues around the urethra or ureter.

31 Claims, 2 Drawing Sheets

CONTROLLED EXPANSION SPHINCTER AUGMENTATION MEDIA

This application is a Divisional of Ser. No. 07/935,151, filed Aug. 20, 1992.

TECHNICAL FIELD

The invention relates to a composition comprising solid polymer particles dispersed in a biodissipatable, generally nonaqueous, solvent. The invention further relates to a method of exerting pressure on a selected tissue structure by inserting into tissues adjacent to the selected tissue structure such a composition. More specifically, the invention provides a treatment for those with urinary incontinence and/or vesicoureteral reflux.

BACKGROUND OF THE INVENTION

Surgical implantation of artificial sphincters has often been employed to treat patients suffering from urinary incontinence. The surgical implantation of the artificial sphincter commonly requires hospitalization. In addition, such a procedure is relatively complex and expensive, and will usually require six to eight weeks of recovery time. Moreover, often time, the procedure is unsuccessful or the artificial sphincter malfunctions. As a result, additional surgery is required to adjust, repair or replace the implant.

In the recent past, urinary incontinence may be successfully treated by using nonsurgical means. The most common and widely used method to treat patients with urinary incontinence is periurethral injection of a composition commercially sold as "Polytef". "Polytef" is a paste comprising a fifty-fifty (50/50) by weight (corresponding to about 64:36 by volume) mixture of glycerine liquid and Teflon particles. However, after injection, over a period of time the glycerine is readily dissipated into the body and then metabolized or eliminated, leaving only the Teflon particles. This means that only fifty (50) percent of the injected weight remains at the injection site. Consequently the surgeon must inject significantly more volume than he thinks he will need and at times must actually close down the urethra further than is desired. This closure could possibly be complete and thus put the patient into temporary urinary retention. Additionally, the fact that a large portion of the volume disappears makes it difficult for the surgeon to visually gauge how much is an appropriate amount of the Teflon paste to inject. As a result, the surgeon is likely to not inject enough paste volume. The procedure therefore may fail, and a second or even a third procedure to inject additional paste may be required. An additional drawback of the Teflon paste is that the Teflon particle size is sufficiently small so as to allow the particles to migrate to other locations of the body such as the lungs, brain, etc. Teflon particles have been known to induce tissue reaction and form Teflon-induced granulomas in certain individuals. This tissue reaction to Teflon has caused concerns for the patient's safety.

An alternative to using the Teflon paste is using a collagen suspension. The collagen suspension is injected in the same manner as Teflon paste so as to form a fibrous mass of tissue around the augmentation site. This fibrous mass created by the collagen injection, however, decreases in size and breaks down over time as it is eventually eliminated by the patient's body. As a result, additional injections are periodically required.

Another alternative which has been investigated but not used other than investigationally is to inject silicone particles dispersed in an aqueous, polyvinylpyrrolidone solution. This combination has the same problem as the Teflon paste in that the polyvinylpyrrolidone solution is readily dissipated away from the area of injection leaving only the volume of silicone particles remaining.

Another material that has been injected is autologous fat. This has had similar problems as the collagen in that the body eventually breaks it down and it disappears.

Devices have been made to attempt to overcome these problems. One device is an inflatable silicone sphere that is passed through a needle and is inflated with saline in the same area that the other materials are injected. There are, however, some problems associated with this devices It is a delicate, mechanical device that is capable of mechanical failure of the valves, shells and structural joints. Another drawback is that the saline filler allows the device to be compliant therefore creating less resistance to the flow of urine. It is also more difficult to place correctly.

Accordingly, it would be desirable to have a composition wherein the mixture is easily administered via injection, generally will not swell or contract to an undesired extent, will be soft enough so as to not cause tissue response/reaction while still being firm enough to provide the required constriction, will not dissipate and will not migrate from the site of injection, thereby enabling the urethra to maintain the initial surgical constriction.

DISCLOSURE OF THE INVENTION

The present invention is directed to overcoming one or more of the problems as set forth above.

One embodiment of the invention is a physiologically acceptable composition comprising a plurality of physiologically acceptable solid polymer particles dispersed in a physiologically acceptable biodissipatable liquid carrier. The solid polymer particles are capable of hydrating, and upon hydration swelling to a predetermined volume. In accordance with a preferred form of this embodiment the liquid carrier is substantially non-aqueous and the solid polymer particles are substantially insoluble in the liquid carrier and in body fluids.

Another embodiment of the invention is a method of exerting pressure on a selected tissue structure by inserting into the tissues adjacent to the tissue structure the above-described physiologically acceptable composition.

Still another embodiment of the invention is a method for increasing urine flow resistance in a patient having urinary incontinence by inserting into the tissues surrounding the patient's urethra, adjacent to the patient's urethral sphincter, the above-described physiologically acceptable composition.

Yet another embodiment of the invention is a method for ureteral augmentation in a patient having vesicoureteral reflux by inserting into the tissues adjacent to the patient's ureteral orifice the above-described physiologically acceptable composition.

Accordingly, the invention provides a nonsurgical, procedure using an easily administered composition for treating patients with urinary incontinence. In addition, the invention obviates the need for re-injections associated with the use of Teflon, collagen, silicone, autologous fat or other similar materials when treating patients with urinary incontinence. By having physiologically acceptable solid polymer particles that will not break down, will not migrate (due to their increased size after swelling) and will not lead to adverse tissue reaction, permanent repair is given to the incontinent patient. Similarly, because of the composition's properties, it can be used to treat patients suffering from vesicoureteral reflux.

BRIEF DESCRIPTION OF THE DRAWINGS

The invention will be better understood by reference to the figures of the drawings wherein like numbers denote like parts throughout and wherein.

BEST MODE FOR CARRYING OUT THE INVENTION

The physiologically acceptable composition can be used in various medical situations. Typically, the physiologically acceptable composition can be injected into tissues adjacent to a selected tissue structure thereby exerting pressure on the selected tissue structure and deforming the selected tissue structure. Preferred uses for this particular application are: 1) to provide a treatment for those with urinary incontinence wherein the urethra cannot be properly constricted to prevent passage of urine from the bladder, and 2) to provide a treatment for those with vesicoureteral reflux wherein the ureter cannot properly constrict to prevent backflow of urine from the bladder up the ureter.

Figure 1:
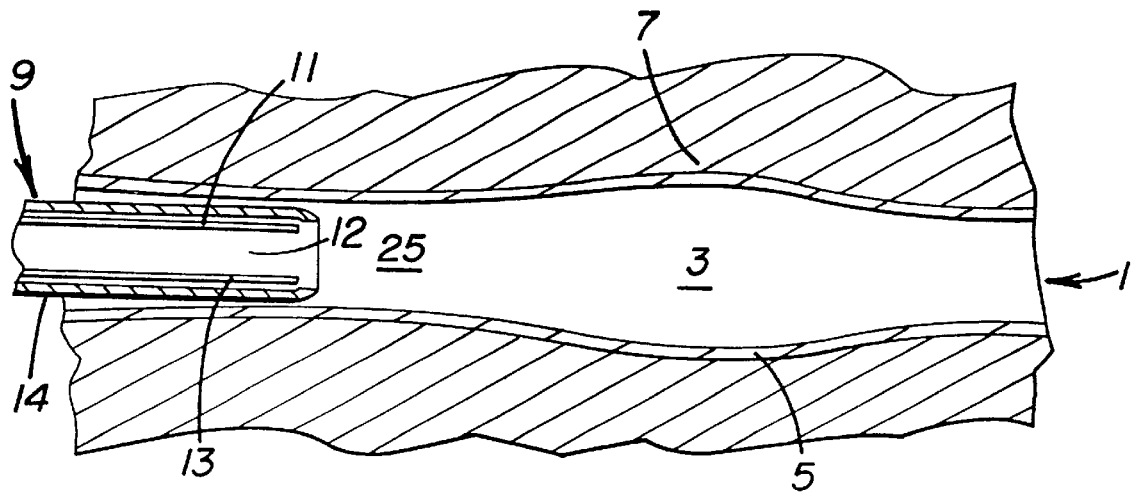
FIG. 1 is a longitudinal section of a tissue structure, more specifically a urethra/ureter, with an enlarged lumen surrounded by muscle tissues.

Referring to FIG. 1, there is shown a urethra/ureter 1 having a wall 5 and an enlarged lumen 3. The urethra/ureter 1 is surrounded by tissues 7. Before the enlarged lumen 3 is to be constricted with the physiologically acceptable composition, a cystoscope 9 comprising a fiberoptic light transmitting element 11, a working channel 12 and a viewing element 13 encased in a metallic sheath 14 is inserted up the urethra/ureter to a distance close to the enlarged lumen 3. The close distance is selected to allow a clear view of the enlarged lumen 3.

Figure 2:
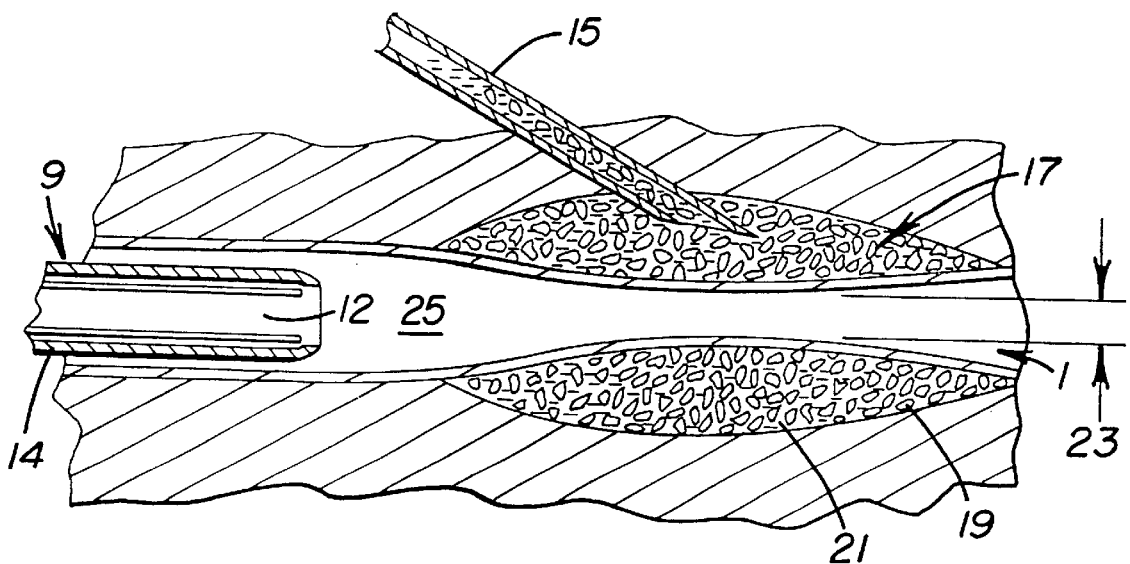
FIG. 2 shows the same longitudinal section immediately after a physiologically acceptable composition has been injected around the enlarged lumen of the urethra using an externally inserted needle technique.

Once the enlarged lumen 3 is readily in view, referring more specifically to FIG. 2, a hypodermic needle 15 is inserted through the tissues 7, preferably over the enlarged lumen 3, stopping near the wall 5 of the enlarged lumen 3. Thereafter, a physiologically acceptable composition 17 is injected via the hypodermic needle 15 into the tissues 7 adjacent the wall 5.

Figure 4:
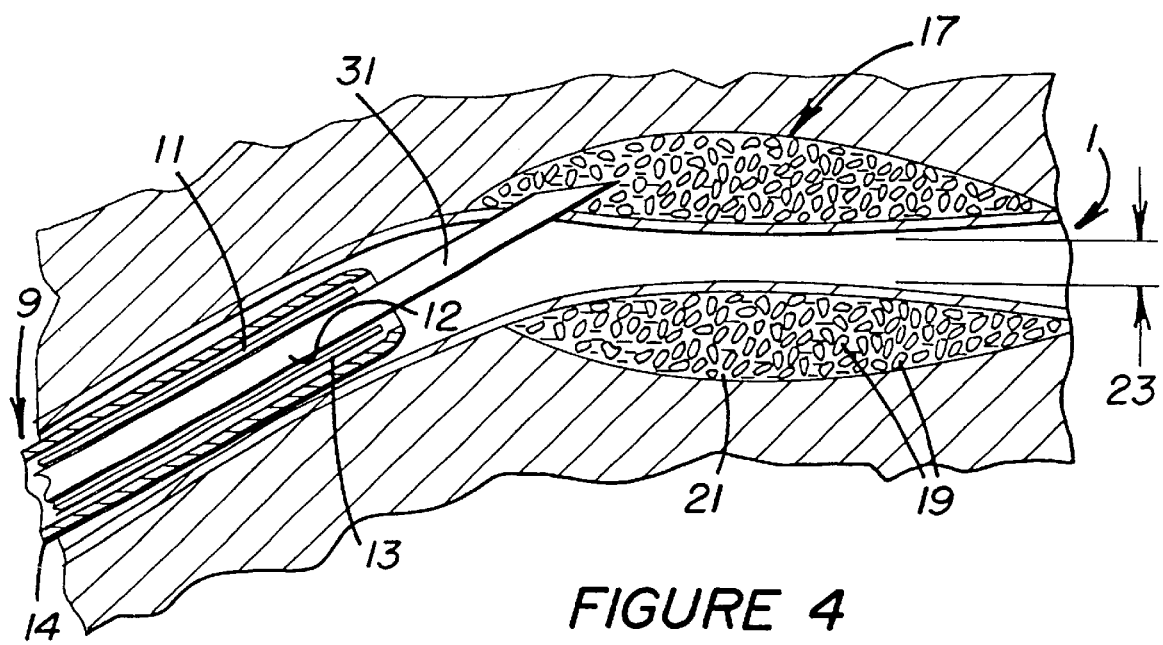
FIG. 4 shows the same longitudinal section as in FIG. 1 immediately after a physiologically acceptable composition has been injected around the enlarged lumen of the urethra/ureter utilizing a through the cystoscope injection technique.

As an alternative, and as is illustrated in FIG. 4, an elongated needle 31 may be inserted through the working channel 12, into the urethra/ureter 1 and the surrounding tissue and the injection can be completed operating solely through the cystoscope 9. This is generally the preferred method of operation, on male patients and is the preferred method for male and female patients for the ureter.

The physiologically acceptable composition 17 comprises plurality of solid polymer particles 19 dispersed in a preferably nonaqueous, physiologically acceptable, biodissipatable liquid carrier 21. The solid polymer particles 19 suitable for the present invention must be physiologically acceptable and are preferably substantially insoluble in the liquid carrier 21 and in body fluids. The solid polymer 19, in a selected concentration, must be able to hydrate and swell to a predetermined volume as the liquid carrier 21 dissipates, the predetermined volume generally being substantially equal to the initial volume of the composition 17.

The solid unhydrated polymer 19 comprises a hydrophilic component and should have a particle size, when unhydrated, which is small enough to allow the formation of a paste which is readily injectable via a needle without significant separation occurring. On hydration occurring following injection the particles preferably attain a particle size sufficient to avoid migration. Migration to other parts of the body should be prevented because the particle may cause tissue reaction. One way of obtaining solid unhydrated polymer particles 19 of the desired size is by cryogenic grinding of a larger piece or pieces of polymer.

The hydrophilic component is suitably a polymer that absorbs at least about 30% water, preferably at least about 50% water, more preferably about 100% water or more, e.g., 150% water, by weight based on the weight of the hydrophilic polymer. The hydrophilic polymer preferably forms a hydrogel on absorption of water. The hydrophilic polymer should not be leachable by body fluids from the site of injection for long periods of time, for example, one year, more preferably two years, still more preferably five years. Most preferably the hydrophilic polymer should be substantially completely non-leachable in that it should preferably be non-leachable for the life of the patient.

The hydrophilic polymer can suitably be selected from the group consisting of poly(ethylene oxide), polyvinyl pyrrolidone, polyvinyl alcohol, poly(propylene oxide), poly (ethylene, glycol), poly(propylene glycol), polytetramethylene oxide, polyacrylamide, poly(hydroxy ethyl acrylate), poly(hydroxy ethyl methacrylate), hydroxy ethyl cellulose, hydroxy propyl cellulose, methoxylated pectin gels, agar, a starch such as cornstarch, a modified starch, an alginate, a hydroxy ethyl carbohydrate, or the like and should preferably be adjusted so as to allow the solid polymer particles 19 to swell to a selected percent after hydration.

The degree of swelling of the polymer can be controlled or tailored as desired by controlling the amount of crosslinking of the polymer. The amount of crosslinking can be adjusted, as is well known in the art, chemically and/or by adjusting the amount of radiation applied to cause the crosslinking. The higher the degree of crosslinking, the less will be the swellability of the hydrated polymer.

If the composition 17 is fifty unit volume liquid carrier 21 and fifty unit volume solid polymer 19, it will generally be desireable to have the solid polymer 19 swell sufficiently upon hydration to compensate for the fifty unit volume lost by dissipation of the liquid carrier 21. It should be noted that this does not generally mean that there should be a 100% increase in volume of the solid polymer 19 since a portion of the liquid carrier is located in interstices between and/or on the particles of polymer whereby the loss of the liquid carrier would result in less than a 50% loss in overall volume. For selected surgeries, it may be desirable to have the expansion volume of the solid polymer 19 exceed or fall short of the initial volume of the injected composition 17. Suitably the expansion percentage can be between about 10% and 1,000%, more usually between about 50% and 250%.

The solid polymer 19 can comprise only a hydrophilic component as indicated previously. However, it will preferably also comprise a non-hydrophilic component. The non-hydrophilic component comprises a polymer which does not substantially absorb or attract water. Preferably, the non-hydrophilic polymeric component is capable of absorbing water in an amount of no more than about 30%, more preferably no more than about 15% and still more preferably no more than about 10%, by weight, based on the weight of the non-hydrophilic polymeric component.

The non-hydrophilic component can be, for example, a thermosetting elastomer such as silicone, a polyurethane such as an aliphatic polyurethane, a polyether polyurethane, a polyester polyurethane; an ethylene copolymer such as ethylene-vinyl acetate copolymer: a polyamide, in particular a polyamide of low crystallinity; an aliphatic polyester; or the like. A particularly preferred non-hydrophilic polymer is a polyurethane, especially an aliphatic polyurethane.

The solid polymer 19, however, can suitably comprise a non-hydrophilic component and a hydrophilic component in a selected ratio. The ratio of the non-hydrophilic component to the hydrophilic component is preferably adjustable so as to allow the solid polymer particles to swell from 50% to 500% after hydration. The hydrophilic component can be selected from the same group indicated above. Similarly, the non-hydrophilic component can be selected from the non-hydrophilic polymeric group previously mentioned.

Examples of swelling (and softening) polymers having both hydrophilic and non-hydrophilic components and which are useful in the practice of the invention are those described in, for example, U.S. Pat. No. 4,883,699, issued Nov. 28, 1989 which is incorporated herein by reference.

The preferred composition for the polymer 19 comprises:

(a) a first phase which comprises a substantially non-hydrophilic polymeric component; and (b) a second phase which comprises a hydrophilic polymeric component;

said material (i) being capable of absorbing water to an extent that it swells with a swelling ratio of at least about 1.3:1, preferably from about 1.5:1 to 3.5:1 (and generally softens with a softening ratio of at least about 2:1)

Also useful are those swelling and softening hydrophilic polymers described in U.S. Pat. Nos. 4,359,558; 4,424,305; 4,454,309 and 4,439,583 of Tyndale Plains-Hunter Ltd. incorporated herein by reference. The preferred polymer composition of these patents essentially comprises a polyurethane diacrylate composition having from about 90 to about 65 weight percent of a hydrophilic polyurethane resin and from about 10 to about 35 weight percent of a diacrylate.

The liquid carrier 21 of the present invention for the above-physiologically acceptable composition 17 is preferably a nonaqueous, physiologically acceptable, biodissipatable liquid carrier. An aqueous liquid carrier can be used but only if it is mixed with the solid polymer particles a sufficiently short time before injection so that the solid polymer particles do not swell significantly prior to and during injection and/or if it hydrates over a sufficiently long period of time so as to allow it to be fully injected before significant, for example, 20% of its ultimate, swelling takes place. If desired, the solid polymer particles can be coated with a physiologically acceptable coating to delay hydration. This is particularly useful when an aqueous liquid serves as the carrier liquid. The term biodissipatable as used herein is defined to mean that the liquid carrier will not remain as such at the location injected but will instead exit that location by any method including, but not limited to, dissolving in body liquids and being carried away, being eliminated, being metabolized, being stored elsewhere, being absorbed by body tissue or by the solid polymer particles in the instance wherein the liquid carrier is aqueous or part aqueous or being volatilized. The biodissipatable liquid carrier 21 further should preferably not act so as to significantly swell the solid polymer particles 19. This property will allow for long term storage of the composition 17. Examples of such biodissipatable liquid carriers are glycerine, glycerol monoacetate, glycerol diacetate, polyethylene glycol, diethylene glycol, polyethylene glycol/polypropylene glycol block copolymers, low molecular weight polyethylene oxides, Polysorbate and mixtures of the above.

The solid polymer 19 is mixed with the biodissipatable liquid carrier 21 in a selected concentration such that the solid polymer 19, upon hydrating in the body when in contact with body fluids, swells to a predetermined volume as the biodissipatable liquid carrier 21 dissipates. The predetermined volume is generally substantially equal to the initial volume of the injected composition. However, if desired, the predetermined volume can be selected to be more or less than the initial volume. It should be noted that the predetermined volume may not be precisely equal to the volume which results within a patient's body when the solid polymer 19 expands since other processes, for example fibrosis, may occur within the body which will lead to a different, usually somewhat larger volume, than would be expected from simply hydrating the solid polymer 19 in vitro. In such a case the size of the predetermined volume can be appropriately adjusted so that the total volume present in the patient's body at the injection site, following hydration, is as desired for the end therapeutic purpose.

As the composition 17 is injected into the tissues 7 adjacent the wall 5 of the enlarged lumen 3, the diameter of the enlarged lumen 3 is observed through the cystoscope 9 for constriction. The composition 17 constricts the wall 5, decreasing the diameter of the once enlarged lumen 3 into a constricted area 23. With increasing volume of the composition 17, the constricted area 23 is further decreased. Once the desired degree of constriction is attained at the constricted area 23, injection of the composition 17 is stopped and the hypodermic needle 15 (or 31) is removed from the site of insertion. The constricted area 23, as observed through the cystoscope 9, would generally have an equal or smaller diameter than the diameter 25 of the rest of the urethra 1. When injections are made about the ureter and when injections are made in males the needle 15 is passed through the working channel 12 of the cystoscope 9 and through the wall of the urethra/ureter rather than through adjacent tissue as illustrated in FIG. 4.

Figure 3:
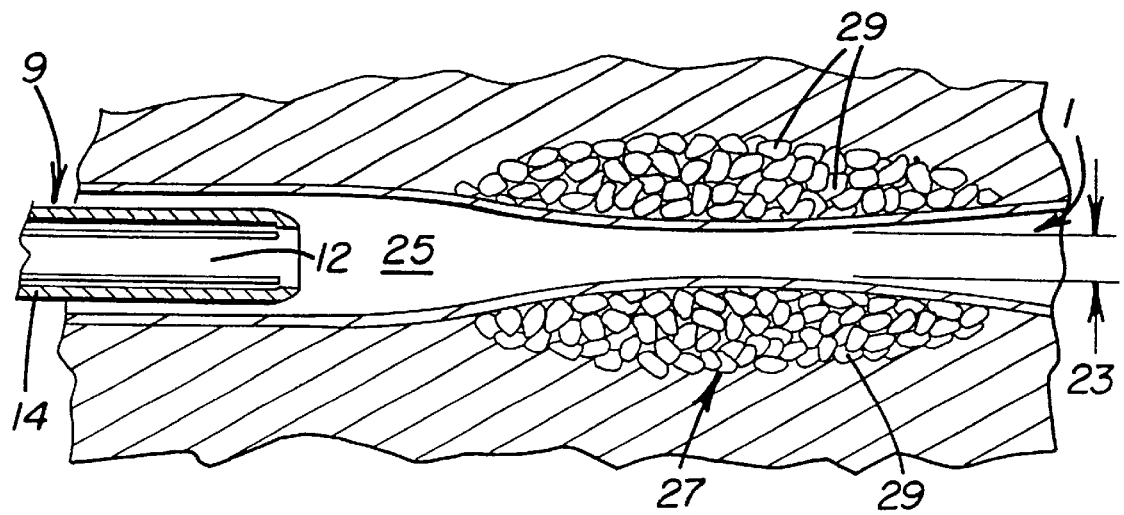
FIG. 3 shows the physiologically acceptable composition wherein the solid polymer particles have hydrated, swelled and agglomerated as the liquid carrier has dissipated.

Referring to FIG. 3, there is shown a solid structure 27 comprising hydrated and-swelled solid polymer particles 29. The solid polymer particles 19 in FIG. 2, after the dissipation of the biodissipatable liquid carrier 21, hydrate and swell to the swelled solid polymer 29 (which may be in the nature of a gel) having a volume which is substantially equal to the sum of the volumes of the dissipated liquid carrier 21 plus the volume of the unswelled solid polymer 19. As a result, the initial volume of the physiologically acceptable composition 17 is maintained. With the initial volume maintained, the constricted area 23 retains the desired degree of constriction. The ability of the solid polymer 19 to hydrate and swell, thereby maintaining the initial volume of the composition 17, therefore eliminates the need for repeated injections to maintain the desired degree of constriction. In addition, since the unswelled solid polymer 19 and the swelled solid polymer 29 are able to remain in place due to their particle size and insolubility in body fluids, the degree of constriction is substantially permanent. Further, the fact that the solid polymer particles 19 swell can lead to their attaining a size such that they resist or prevent migration from the site of injection. The literature is unclear in this area but appears to indicate that particles of 50 micron or 80 microns in size will resist migration.

It should be noted that swelling in length (diameter in spherical particles) is proportional to the cube root of swelling in volume. Thus, very large swelling ratios may be desirable in certain instances so as to allow the composition to be prepared in readily injectable paste form while still providing swelled polymer particles of a size which will resist migration from the injection site.

In certain situations it can be desireable to add a radiopaque material to the solid polymer particles, preferably barium sulfate, bismuth subcarbonate, tantalum, tungsten, silver or mixtures thereof. The radiopaque material can be incorporated into the solid polymer from which the solid polymer particles are formed by melt mixing or, in the case of gels by dispersing into the gels prior to crosslinking them. By having the solid polymer particles radiopaque, the constricted site 23, normally radiolucent to X-rays as with many other body tissues, will no longer be radiolucent. Consequently, the constricted area 23 can be examined by X-ray imaging or fluoroscopy which may help to visualize the internal shape within the tissue since this cannot be seen by direct observation through the cystoscope 9.

Industrial Applicability

Although the physiologically acceptable composition is typically inserted into tissues adjacent to a tissue structure to exert pressure on the selected tissue structure, a specific use for the composition is for increasing urine flow resistance in patients having urinary incontinence. The physiologically acceptable composition is inserted into the tissues surrounding the patient's urethra adjacent to the patient's urethral sphincter. The presence of the physiologically acceptable composition allows constriction of the urethra thereby decreasing urine flow from the bladder. As a result the incontinent patient will have an improved control of urine flow.

The physiologically acceptable composition can also be used in patients having vesicoureteral reflux. Similar to the method used in increasing urine flow resistance in patients having urinary incontinence, the physiologically acceptable composition is injected into the tissues adjacent to the patient's ureteral orifice thereby constricting the ureteral duct. With the constriction, the undesirable backflow of urine from the bladder up the ureter is prevented.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A method of deforming a selected tissue structure comprising inserting into tissues adjacent the selected tissue structure and into contact with body fluids, a selected volume of a physiologically acceptable composition comprising a plurality of physiologically acceptable relatively hard solid hydrophilic polymer particles dispersed in a physiologically acceptable biodissipatable liquid carrier, the plurality of solid polymer particles, prior to being positioned in contact with body fluids having a volume which is less than a predetermined volume, and hydrating following being positioned in contact with body fluids and on hydration absorbing at least about 30 wt % water based on weight of the solid hydrophilic polymer particles, softening and swelling to assume the predetermined volume and being substantially insoluble in body fluids.

2. A method as set forth in claim 1 whereby the plurality of solid polymer particles hydrates and swells to the predetermined volume as the liquid carrier dissipates, the predetermined volume being substantially equal to the selected volume.

3. A method as set forth in claim 1 including controlling the amount of the composition inserted and terminating insertion when the desired amount has been inserted.

4. A method as set forth in claim 1 wherein the solid polymer particles have a particle size of greater than 25 microns whereby the polymer is prevented from migrating.

5. A method as set forth in claim 1 herein the liquid carrier is non aqueous and wherein the solid polymer particles are substantially insoluble in the non aqueous liquid carrier.

6. A method for increasing urine flow resistance in a patient having urinary incontinence comprising inserting into tissues surrounding the patient's urethra and into contact with body fluids, a selected volume of a physiologically acceptable composition comprising a plurality of physiologically acceptable solid hydrophilic polymer particles dispersed in a physiologically acceptable biodissipatable liquid carrier, the plurality of solid polymer particles, prior to being positioned in contact with body fluids having a volume which is less than a predetermined volume, hydrating following being positioned in contact with body fluids and on hydration absorbing at least about 30 wt % water based on weight of the solid hydrophilic polymer particles and swelling to assume the predetermined volume and being substantially insoluble in body fluids.

7. A method as set forth in claim 6 whereby the solid polymer particles hydrates and swells to the predetermined volume as the liquid carrier dissipates, the predetermined volume being substantially equal to the selected volume.

8. A method as set forth in claim 6 including controlling the amount of the composition inserted as to constrict the urethra to a desired degree, thereby increasing urine flow resistance.

9. A method as set forth in claim 6 further including inserting into the urethra an observation device to allow monitoring the constriction of the urethra as the composition is inserted.

10. A method as set forth in claim 6 wherein the solid polymer particles having a particle size of greater than 25 microns whereby the polymer is prevented from migrating.

11. A method as set forth in claim 6, wherein the liquid carrier is non aqueous and wherein the solid polymer particles are substantially insoluble in the non aqueous liquid carrier.

12. A method for treating a patient having vesicoureteral reflux comprising inserting into tissues adjacent the patient's ureteral orifice and into contact with body fluids, a selected volume of a physiologically acceptable composition comprising a plurality of physiologically acceptable solid hydrophilic polymer particles in a physiologically acceptable biodissipatable liquid carrier, the plurality of solid polymer particles, prior to being positioned in contact with body fluids having a volume which is less than a predetermined volume, hydrating following being positioned in contact with body fluids and on hydration absorbing at least about 30 wt % water based on weight of the solid hydrophilic polymer particles and swelling to assume the predetermined volume and being substantially insoluble in body fluids.

13. A method as set forth in claim 12 whereby the solid polymer particles hydrates and swells to the predetermined volume as the liquid carrier dissipates, the predetermined volume being substantially equal to the selected volume.

14. A method as set forth in claim 12 including controlling the amount of the composition inserted as to constrict the ureter to a desired degree, thereby decreasing urine backflow.

15. A method as set forth in claim 12 further including inserting into the ureter an observing device to allow monitoring the constriction of the ureter as the composition is inserted.

16. A method as set forth in claim 12 wherein the solid polymer particles having a particle size of greater than 25 microns whereby the polymer is prevented from migrating.

17. A method as set forth in claim 12, wherein the liquid carrier is non aqueous and wherein the solid polymer particles are substantially insoluble in the non aqueous liquid carrier.

18. A method of deforming a selected tissue structure comprising inserting into tissues adjacent the selected tissue structure a selected volume of a physiologically acceptable composition comprising a plurality of physiologically acceptable solid polymer particles dispersed in a physiologically acceptable biodissipatable liquid carrier, the plurality of solid polymer particles, prior to being positioned adjacent the selected tissue structure having a volume which is less than a predetermined volume, and swelling, following being positioned adjacent the selected tissue structure, to assume the predetermined volume and being substantially insoluble in body fluids.

19. A method as set forth in claim 18 whereby the plurality of solid polymer particles swells to the predetermined volume as the liquid carrier dissipates, the predetermined volume being substantially equal to the selected volume.

20. A method as set forth in claim 18 including controlling the amount of the composition inserted and terminating insertion when the desired amount has been inserted.

21. A method as set forth in claim 18 wherein the liquid carrier is non aqueous.

22. A method for increasing urine flow resistance in a patient having urinary incontinence comprising inserting into tissues surrounding the patient's urethra a selected volume of a physiologically acceptable composition comprising a plurality of physiologically acceptable solid polymer particles dispersed in a physiologically acceptable biodissipatable liquid carrier, the plurality of solid polymer particles, prior to being positioned in tissues surrounding the patient's urethra having a volume which is less than a predetermined volume, swelling to assume the predetermined volume following insertion and being substantially insoluble in body fluids.

23. A method as set forth in claim 22 whereby the solid polymer particles swells to the predetermined volume as the liquid carrier dissipates, the predetermined volume being substantially equal to the selected volume.

24. A method as set forth in claim 22 including controlling the amount of the composition inserted as to constrict the urethra to a desired degree, thereby increasing urine flow resistance.

25. A method as set forth in claim 22 wherein the liquid carrier is non aqueous.

26. A method for treating a patient having vesicoureteral reflux comprising inserting into tissues adjacent the patient's ureteral orifice a selected volume of a physiologically acceptable composition comprising a plurality of physiologically acceptable solid polymer particles in a physiologically acceptable biodissipatable liquid carrier, the plurality of solid polymer particles, prior to being positioned adjacent the patient's ureteral orifice having a volume which is less than a predetermined volume and swelling to assume the predetermined volume following insertion and being substantially insoluble in body fluids.

27. A method as set forth in claim 26 whereby the solid polymer particles hydrates and swells to the predetermined volume as the liquid carrier dissipates, the predetermined volume being substantially equal to the selected volume.

28. A method as set forth in claim 26 including controlling the amount of the composition inserted as to constrict the ureter to a desired degree, thereby decreasing urine backflow.

29. A method as set forth in claim 26 wherein the liquid carrier is non aqueous.

30. A method of deforming a selected tissue structure comprising inserting into tissues adjacent the selected tissue structue a selected volume of a physiologically acceptable composition comprising a plurality of substantially unswollen physiologically acceptable solid polymer particles dispersed in a physiologically acceptable biodissipatable liquid carrier, the plurality of solid polymer particles, prior to being positioned adjacent the selected tissue structure having a volume which is less than a predetermined volume, and swelling, following being positioned adjacent the selected tissue structure, to assume the predetermined volume and being substantially insoluble in body fluids.

31. A method for exerting pressure on a selected tissue structure comprising inserting into tissues adjacent the selected tissue structure a selected volume of a physiologically acceptable composition comprising a plurality of physiologically acceptable solid polymer particles which are capable of absorbing water upon being inserted adjacent the selected tissue structure and of, upon absorbing water, swelling and are dispersed in a physiologically acceptable biodissipatable liquid carrier, the plurality of solid polymer particles, prior to being positioned adjacent the selected tissue structure having a volume which is less than a predetermined volume, and swelling, following being positioned adjacent the selected tissue structure, to assume the predetermined volume and being substantially insoluble in body fluids.

* * * * *

UNITED STATES PATENT AND TRADEMARK OFFICE
CERTIFICATE OF CORRECTION

PATENT NO. : 6,306,418 B1 Page 1 of 1
DATED : October 23, 2001
INVENTOR(S) : Robert Steven Bley It is certified that error appears in the above-identified patent and that said Letters Patent is hereby corrected as shown below:

Column 10,
Line 40, please delete "for" and insert therefore -- of --

Signed and Sealed this

Fifteenth Day of June, 2004

JON W. DUDAS
*Acting Director of the United States Patent and Trademark Office*